(12) United States Patent
Scheuering

(10) Patent No.: US 7,040,807 B2
(45) Date of Patent: May 9, 2006

(54) RADIOGRAPHIC IMAGE ACQUISITION APPARATUS WITH PULSED LASER LIGHT MARKER

(75) Inventor: Peter Scheuering, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/834,433

(22) Filed: Apr. 29, 2004

(65) Prior Publication Data
US 2004/0258211 A1 Dec. 23, 2004

(30) Foreign Application Priority Data
Apr. 29, 2003 (DE) .............................. 103 19 327

(51) Int. Cl.
*A61B 6/08* (2006.01)

(52) U.S. Cl. ...................... 378/206; 606/130; 600/426; 356/399

(58) Field of Classification Search ........ 378/204–206; 606/130; 600/426; 356/399
See application file for complete search history.

(56) References Cited

U.S. PATENT DOCUMENTS

| | | | | | |
|---|---|---|---|---|---|
| 4,502,147 | A | * | 2/1985 | Michaels | 378/206 |
| 5,577,095 | A | * | 11/1996 | Kobayashi | 378/206 |
| 6,104,778 | A | * | 8/2000 | Murad | 378/65 |
| 6,782,012 | B1 | * | 8/2004 | Karasaki et al. | 372/10 |
| 2002/0180988 | A1 | * | 12/2002 | Johnston et al. | 356/602 |

\* cited by examiner

*Primary Examiner*—Craig E. Church
*Assistant Examiner*—Krystyna Suchecki
(74) *Attorney, Agent, or Firm*—Schiff Hardin LLP

(57) ABSTRACT

An apparatus for radiographic image acquisition has a radiation source with an associated laser device for representation of a linear light marking on the examination subject to align the subject relative to the radiation source for a subsequent image acquisition. The laser of the laser device is operated pulsed with a pulse-pause ratio of 1:n, with n>1.

13 Claims, 1 Drawing Sheet

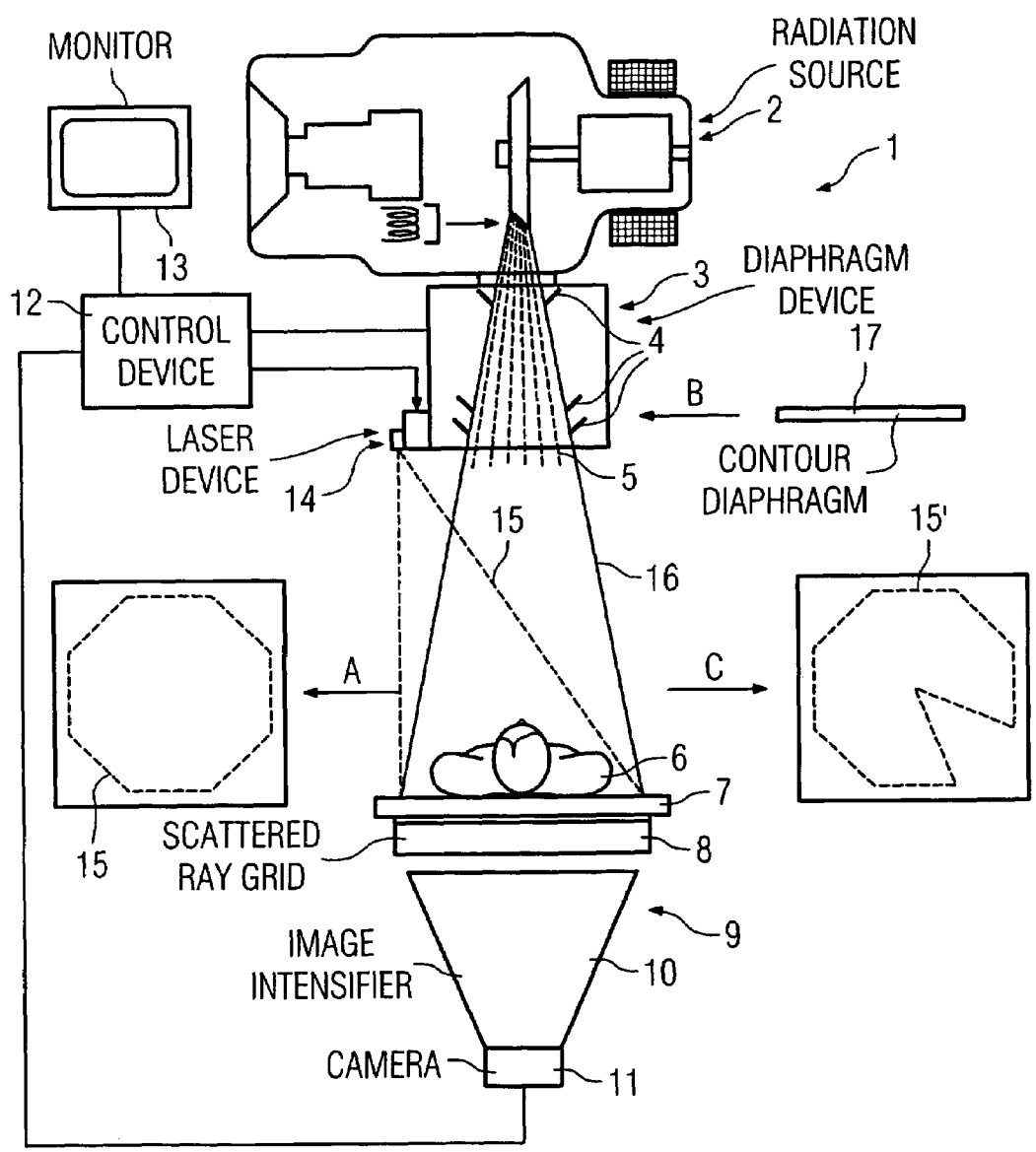

RADIOGRAPHIC IMAGE ACQUISITION APPARATUS WITH PULSED LASER LIGHT MARKER

BACKGROUND OF THE INVENTION

1. Field of the Invention

The present invention concerns an apparatus for radiographic image acquisition, having a radiation source with an associated laser device to display a linear light marking on the examination subject for alignment of the subject relative to the radiation source for a subsequent image acquisition.

2. Description of the Prior Art

In the acquisition of radiographic images, for example x-ray images, the precise alignment of the patient relative to the radiation source (the x-ray radiator) is very important so that the correct examination region is acquired by the radiation image and the patient is not exposed unnecessarily frequently to the radiation due to erroneous positioning. For alignment purposes, in order to make the body region irradiated by the x-ray radiation recognizable in a subsequent image exposure, in the prior art a light-beam localizer is used in which light generated by a strong halogen lamp having a power of more than 100 watts is projected on the patient. A disadvantage of such a light-beam localizer is that the halogen lamps frequently burn out due to significant heating. A further disadvantage is that, in the case of the radiation image acquisition apparatus being in a room with strong ambient brightness (such as, for example, in an operating room), the projected light field is only very poorly visible due to the ambient brightness.

As an alternative to the halogen light-beam localizer, the use of a laser-line light-beam localizer is known in which a narrow laser line is superimposed on the patient by means of a laser in the center of the expected x-ray beam field. This laser-line light-beam localizer namely allows a positioning of the patient without having to activate x-ray radiation for this purpose. Due to the fact that lasers that can be aimed on humans may not exceed a specific low power, the resulting laser line projection is relatively weak. Problems result from this when the laser light line is projected in brightly illuminated spaces, since it only visible with great difficulty.

SUMMARY OF THE INVENTION

An object of the invention is to provide an apparatus that allows a clear marking using a laser light-beam localizer apparatus, even given stronger ambient brightness.

This object is achieved in accordance with the invention by an apparatus of the initially cited type wherein the laser of the laser device is operated in pulsed fashion with a pulse-pause ratio of 1:n, with n>1.

The inventive pulsed operation, with the laser being intermittently activated and deactivated, offers the possibility to use a laser with an n-multiple higher power. By virtue of the pulse operation, the average power is equal to the power without pulses, thus given continuous laser operation. As a result of the pulsed operation, a solid line is not projected on the patient, but instead an interrupted line, with the illuminated line sections having a ratio of 1:n to the non-illuminated locations. The illuminated line segments, however, are substantially brighter, namely n-times as bright as in the continuous, non-pulsed operation. Overall, a substantially brighter display of the marking on the examination subject is achieved, with an interrupted, dashed line being formed due to the pulsed operation. Due to the clearly brighter display of the light marking, it is also clearly recognizable in a strongly illuminated environment, such that the doctor or the x-ray assistant can effect substantially more simply the positioning of the patient with the aid of the light marking.

The pulse-pause ratio is, as specified, 1:n, whereby n preferably is $\geq 2$ and $\leq 10$, in particular $\leq 8$.

In an embodiment of the invention, the laser device has one or more deflection mirrors operated by a control device with a frequency >100 Hz for deflecting the laser beam, with which the pulsed laser beam is projected on the examination subject and with which the line form is generated. The frequency should be selected such that the light marking is shown in the form of lines or line segments with a length $\geq 0.5$ cm and preferably $\leq 5$ cm, in particular $\geq 2$ cm. The larger the selected n, the shorter the line segments.

In an embodiment of the invention, the control device immediately shuts down the laser given stoppage of one or all deflection mirrors. This safety measure ensures that the laser beam is not still directed on the patient given failure of one or all deflection mirrors, since failure of all deflection mirrors would result in the laser beam no longer being moved, and instead would be projected on a fixed point, which must be prevented.

In a further embodiment, a light marking showing the subject region (gated by a diaphragm device associated with the radiation source) can be shown on the subject by means of the laser. This embodiment enables the actual subject region irradiated with x-ray radiation to be framed with the laser, or the region border to be shown with the light marking. Not only straight lines but almost any geometric shape can be reproduced by means of the deflection mirrors.

Because the size and shape of the subject region that is irradiated with x-ray radiation is defined by the diaphragm device (associated with and downstream from the radiation source) which delimits the edges of the beam cone, the invention allows the laser to show, with the light marking, the subject region border defined by the diaphragm setting, such that the doctor or the x-ray assistant can very clearly recognize the entire subject region due to the greater marking brightness.

The laser device can be arranged externally of the diaphragm device, with the control device operating the deflection mirror or mirrors dependent on the position data of the diaphragm device. The diaphragm plates can be modified either manually or by remote control, but in any case the set diaphragm position data (that are ultimately a measure for the size and shape of the irradiated region) are available to the control device. The deflection mirrors of the laser device are controlled dependent on this diaphragm position data, such that the surface framing of the actual irradiated surface can be shown precisely.

For radiation image acquisition, not only is the diaphragm device (directly downstream from the radiation source) operated by adjusting the diaphragm plates, but sometimes it is necessary to move a specific contour diaphragm into the beam path. This is for preventing exposure of specific body regions to avoid over irradiation. Wedge contour diaphragms, finger contour diaphragms or heart contour diaphragms are examples. These diaphragms are moved into the beam path between the source and the detector. By means of such contour diaphragms, the shape of the surface area irradiated with radiation (which is originally defined by adjustment of the plate diaphragm device) also changes. Nevertheless, in order to be able to show to the doctor or the x-ray assistant the actual surface area or the actual resulting surface shape, in an embodiment the control device operates the deflection mirror or mirrors dependent on the position and/or shape of a contour diaphragm moved into the beam path. If such a contour diaphragm (which is normally inserted in the diaphragm device) is brought into the beam path, a sensor or detector automatically recognizes the type of the inserted contour diaphragm. From this information, control device accesses appropriate position and/or shape data for this contour diaphragm, and the control of the deflection mirror or mirrors ensues using that data in order to be able to show precisely the actual shape (resulting from the cooperation of the diaphragm plates and the contour diaphragm) of the surface and (due to the pulsed operation) very brightly and thus easy to recognize.

DESCRIPTION OF THE DRAWING

The single FIGURE is a schematic illustration of a radiographic image acquisition apparatus constructed and operating in accordance with the present invention.

DESCRIPTION OF THE PREFERRED EMBODIMENTS

The figure shows an inventive radiographic image acquisition apparatus 1 having a radiation source 2 (here an x-ray radiator) downstream from which is a diaphragm device 3 (here a depth diaphragm) having a number of diaphragm plates 4 with which the shape of the x-ray beam 5 emitted by the radiation source 2 can be defined. The shape and the size of the surface of the patient that is irradiated with the x-ray radiation 5 is also thus defined. The patient 6 lies on a patient table 7, downstream from which is a scattered-ray grid 8. The image acquisition ensues with a radiation detector 9, here an image intensifier 10 with a downstream camera 11. To control the image generation and acquisition operation, a control device 12 with downstream monitor 13 is provided, on which an acquired radiation image is displayed.

In order to be able to show the surface region that is irradiated on the patient dependent on the setting of the diaphragm device 3, a laser device 14 having a laser with an associated oscillating mirror mechanism is provided. The oscillating mirror mechanism has a number of separately operable deflection mirrors. The operation of the laser device 14, i.e. the oscillation or deflection mirror thereof, is controlled by the control device 12. The laser is controlled to operate pulsed meaning it is intermittently switched on and off. The pulse-pause ratio is 1:n, the frequency is preferably >100 Hz. n is selected in from the approximate interval 2 to 8.

Depending on how the deflection mirrors are operated, it is possible to show different geometric line shapes on the patient 6. It is possible to show only a straight line, as was the case with conventional laser line light-beam localizers, this line designating the center of the expected x-ray beam field. An interrupted line, however, results due to the pulse operation, and—because a laser with n-times higher power can be used as a consequence of the pulsed operation—in comparison to laser light-beam localizers used in the prior art with continuous non-pulsed operation, the line segments are clearly brighter, namely n-times as bright.

Alternatively to the representation of a straight line, it is also possible to control the deflection mirrors such that the exact framing of the shape of the beam of x-ray radiation 5 (defined by the setting of the diaphragms plates 4 of the diaphragm device 3 can be shown. The position data for the diaphragm plates 4 are known to the control device 12. Either the diaphragm plates 4 can be manually adjusted at the diaphragm device, or the position data are given to the control device 12 via a communication line, or the diaphragm plates 4 can be set by the control device 12 by remote control. The size of the resulting irradiated surface thus is also known from this position data and the known distance of the radiation source 2 from the patient table. These data, thus the film-focus distance and the diaphragm position data, are the control parameters, depending on which the control of the deflection mirrors ensues. As shown in the FIGURE, the generated laser light line 15 corresponds to the greatest possible extent with the edge of the radiation cone 16. For example, the laser light line 15 (that is shown dashed in the left displayed view to which the arrow A points) is now shown that results from the diaphragm setting in connection with the film-focus distance. For example, an octagonal shape results here, due to gating known as an ids gating (octagon gating). The laser light line 15 is dashed; it is thus an interrupted line. The frequency with which the deflection mirrors are operated should be selected such that a line length of 0.5 to 2 cm results given the selected n-value.

With the inventive pulsed laser device 14, it is possible to be able to generate arbitrary geometric line shapes. Moreover, it is also possible to insert into the beam path a contour diaphragm 17, corresponding to which a receptacle (not shown in detail) is provided at the housing of the diaphragm device 3. The type of the inserted contour diaphragm 17 can be detected by the control device 12 via electronic recognition means (not shown), based upon which the control device 12 can select the appropriate contour diaphragm-specific position and shape data that can be used to control the laser device 14. Such a contour diaphragm 17, that (as specified by the arrow B) is positioned below the diaphragm device 3, is shown as an example in the FIGURE, as a wedge diaphragm, The diaphragm device 17 is transparent except in one wedge-shaped area, which causes the radiation beam 16 to be additionally changed with regard to its shape by the diaphragm 17. The wedge-shaped area in which the contour diaphragm 17 is not transparent blanked out. The position and shape data of the wedge diaphragm 17 are known to the control device 12; so it can control the laser device 14 that is arranged externally on the housing of the diaphragm device 3. The line shape 15' resulting from this control is shown in the extracted top view indicated by the arrow C. The wedge-shaped excerpt that is defined by the contour diaphragm 17 can be seen. The actual area that is irradiated with x-ray radiation 5 was thus correspondingly changed. This change can be immediately and unambiguously made visible by means of the laser device 14.

As shown in the FIGURE the laser device 14 is arranged externally on the housing of the diaphragm device 3, This side attachment does not disturb a dosage meter chamber that is arranged in the beam path nor possible inserted metal filters or the like. The heat development is low, such that no heating leading to a failure of the laser device 14 needs to be countered. A further advantage of the laser device 14 is that the imaging is sharp, in contrast in particular to the conventionally used halogen light-beam localizer. A halogen lamp has a coil helix that, in order to achieve a sharp image, has to be extremely small. In contrast to this, the laser light beam can be made sharp by suitable focusing with optics associated with the laser. Automated tracking of changes in the film-focus spacing is possible, meaning that when this distance changes, a new sharp line setting is realized by automatic adjustment of the optics.

Although modifications and changes may be suggested by those skilled in the art, it is the intention of the inventor to embody within the patent warranted hereon all changes and modifications as reasonably and properly come within the scope of his contribution to the art.

I claim as my invention:

1. A radiographic image acquisition apparatus comprising:
   a radiation source for emitting a radiation beam adapted to irradiate an examination subject;
   a radiation detector disposed for detecting radiation in said radiation beam after penetrating examination subject; and
   a laser device for producing a linear light marking on the examination subject for assisting in aligning said examination subject with said radiation source, said laser device comprising a laser and an operating unit for said laser for pulsing said laser with a pulse-pause ratio of 1:n, with n>1.

2. An apparatus as claimed in claim 1 wherein said operating unit pulses said laser with said pulse-pause ratio of 1:n, with n>2.

3. An apparatus as claimed in claim 1 wherein said operating unit pulses said laser with said pulse-pause ration of 1:n, with $2 \leq n \leq 10$.

4. An apparatus as claimed in claim 1 wherein said operating unit pulses said laser with said pulse-pause ration of 1:n, with $2 \leq n \leq 8$.

5. An apparatus as claimed in claim 1 wherein said laser emits a laser beam, and wherein said laser device comprises at least one deflecting mirror disposed for deflecting said laser beam from said laser onto said examination subject and wherein said apparatus comprises a control device for operating said at least one deflection mirror with a deflection frequency greater than 100 Hz.

6. An apparatus claimed in claim 5 wherein said control device operates said at least one deflection mirror with a deflection frequency for producing said linear light marking on said examination subject as a plurality of lines each having a length $\geq 0.5$ cm.

7. An apparatus as claimed in claim 6 wherein said control device operates said at least one deflection mirror with a deflection frequency for producing said linear light marking on said examination subject as a plurality of lines each having a length $\geq 0.5$ cm and $\leq 5$ cm.

8. An apparatus as claimed in claim 6 wherein said control device operates said at least one deflection mirror with a deflection frequency for producing said linear light marking on said examination subject as a plurality of lines each having a length $\geq$ cm and $\leq 2$ cm.

9. An apparatus as claimed in claim 5 wherein said control device detects an occurrence of a failure of said at least one deflection mirror, and wherein said control device is connected to said operating device for immediately shutting off said operating device and thereby ceasing operation of said laser if said failure is detected.

10. An apparatus as claimed in claim 5 comprising a diaphragm device disposed in said radiation beam and having a plurality of diaphragm plates, said diaphragm plates being respectively adjustable by said control device for gating said radiation beam to produce a delimited region of said examination subject that is irradiated by said radiation beam, and wherein said linear light marking generated by said laser device designates said delimited region on the examination subject.

11. An apparatus as claimed in claim 10 wherein said laser device is disposed externally of said diaphragm device, and wherein said diaphragm device generates position data identifying respective positions of said diaphragm plates, and wherein said control device operates said deflection mirror dependent on said position data for causing said linear light marking to designate said delimited region.

12. An apparatus as claimed in claim 10 wherein said diaphragm device includes a contour diaphragm movable into and out of said radiation beam, and wherein said diaphragm device generates contour diaphragm data indicating at least one of a position and shape of said contour diaphragm, and wherein said control unit is supplied with said contour diaphragm data from said diaphragm device and controls said at least one deflection mirror dependent on said contour diaphragm data when said contour diaphragm is in said radiation beam.

13. An apparatus as claimed in claim 1 comprising a diaphragm device disposed in said radiation beam and having a plurality of diaphragm plates, said diaphragm plates being respectively adjustable by said control device for gating said radiation beam to produce a delimited region of said examination subject that is irradiated by said radiation beam, and wherein said linear light marking generated by said laser device designates said delimited region on the examination subject.

* * * * *